United States Patent [19]
Klein

[11] Patent Number: 6,162,960
[45] Date of Patent: Dec. 19, 2000

[54] COMPRESSION SPONGE FOR WOUND CARE

[76] Inventor: Jeffrey A. Klein, 30280 Rancho Viejo Rd., San Juan Capistrano, Calif. 92675

[21] Appl. No.: 09/236,521

[22] Filed: Jan. 25, 1999

[51] Int. Cl.[7] .................................................. A61F 13/00
[52] U.S. Cl. ............................................. 602/41; 602/44
[58] Field of Search ................................ 602/41, 47, 49, 602/50, 54, 44

[56] References Cited

U.S. PATENT DOCUMENTS

| | | | |
|---|---|---|---|
| 808,433 | 12/1905 | Cartledge . | |
| 3,157,178 | 11/1964 | Bentov | 128/156 |
| 3,279,465 | 10/1966 | Cherio et al. | 128/171 |
| 3,824,996 | 7/1974 | Carlisle | 128/156 |
| 3,871,378 | 3/1975 | Duncan et al. | 128/290 |
| 3,888,248 | 6/1975 | Moore et al. | 128/156 |
| 3,929,135 | 12/1975 | Thompson | 128/287 |
| 3,967,623 | 7/1976 | Butterworth et al. | 128/287 |
| 3,968,803 | 7/1976 | Hyman | 128/482 |
| 4,282,874 | 8/1981 | Mesek | 128/287 |
| 4,341,216 | 7/1982 | Obenour | 128/287 |
| 4,347,844 | 9/1982 | Ohki et al. | 128/287 |
| 4,400,832 | 8/1983 | Kinder | 2/406 |
| 4,645,500 | 2/1987 | Steer | 604/378 |
| 4,665,909 | 5/1987 | Trainor | 128/155 |
| 4,681,577 | 7/1987 | Stern et al. | 604/378 |
| 4,829,987 | 5/1989 | Stewart | 128/65 |
| 4,835,795 | 6/1989 | Lonon | 2/408 |
| 4,937,273 | 6/1990 | Okayama et al. | 521/119 |
| 5,009,652 | 4/1991 | Morgan et al. . | |
| 5,054,129 | 10/1991 | Baehr | 2/409 |
| 5,060,315 | 10/1991 | Ewing | 2/69 |
| 5,281,208 | 1/1994 | Thompson et al. | 604/378 |
| 5,348,547 | 9/1994 | Payne et al. | 604/378 |
| 5,352,217 | 10/1994 | Curro | 604/378 |
| 5,429,593 | 7/1995 | Matory | 602/79 |
| 5,449,352 | 9/1995 | Nishino et al. | 604/383 |
| 5,478,335 | 12/1995 | Colbert | 604/383 |
| 5,681,579 | 10/1997 | Freeman | 424/448 |

FOREIGN PATENT DOCUMENTS 2519865  7/1983  France .

OTHER PUBLICATIONS

"The Tumescent Technique—Anesthesia and Modified Liposuction Technique", by Jeffrey Alan Klein, M.D., Dermatologic Clnics, vol. 8, No. 3, Jul. 1990, 13 pages.

"The Tumescent Technique for Lipo–Suction Surgery", by Jeffrey A. Klein, M.D., Am. J. Cosmetic Surg., vol. 4, No. 4, 1987, 5 pages.

"Tumescent Technique for Regional Anesthesia Permits Lidocaine Doses of 35 mg/kg for Liposuction", by Jeffrey A. Klein, M.D., J. Dermatol. Surg. Oncol., 16:3, Mar. 1990, 16 pages.

"Tumescent Technique for Local Anesthesia Improves Safety in Large–Volume Liposuction", by Jeffrey A. Klein, M.D., Plastic and Reconstructive Surgery, vol. 92, No. 6, Nov. 1993, 15 pages.

*Primary Examiner*—Michael A. Brown
*Assistant Examiner*—Lalita M. Hamilton
*Attorney, Agent, or Firm*—Stetina Brunda Garred & Brucker

[57] ABSTRACT

A compression sponge for wound care operable in the collection of liquid emanating from a wound site. The pad has at least one generally uniform bibulous layer operable as a wick to absorb, generally uniformly distribute there through, and retain liquid whereby such uniform liquid distribution throughout the entire layer provides uniform pressure distribution of any externally applied pressure on the pad. A liquid-permeable sheet such as a non-interacting, liquid-permeable paper product is disposed on the surface of the bibulous layer to interface with the wound site, while a liquid impermeable sheet with wrap-around edges prevents leakage of liquid from the pad.

15 Claims, 1 Drawing Sheet

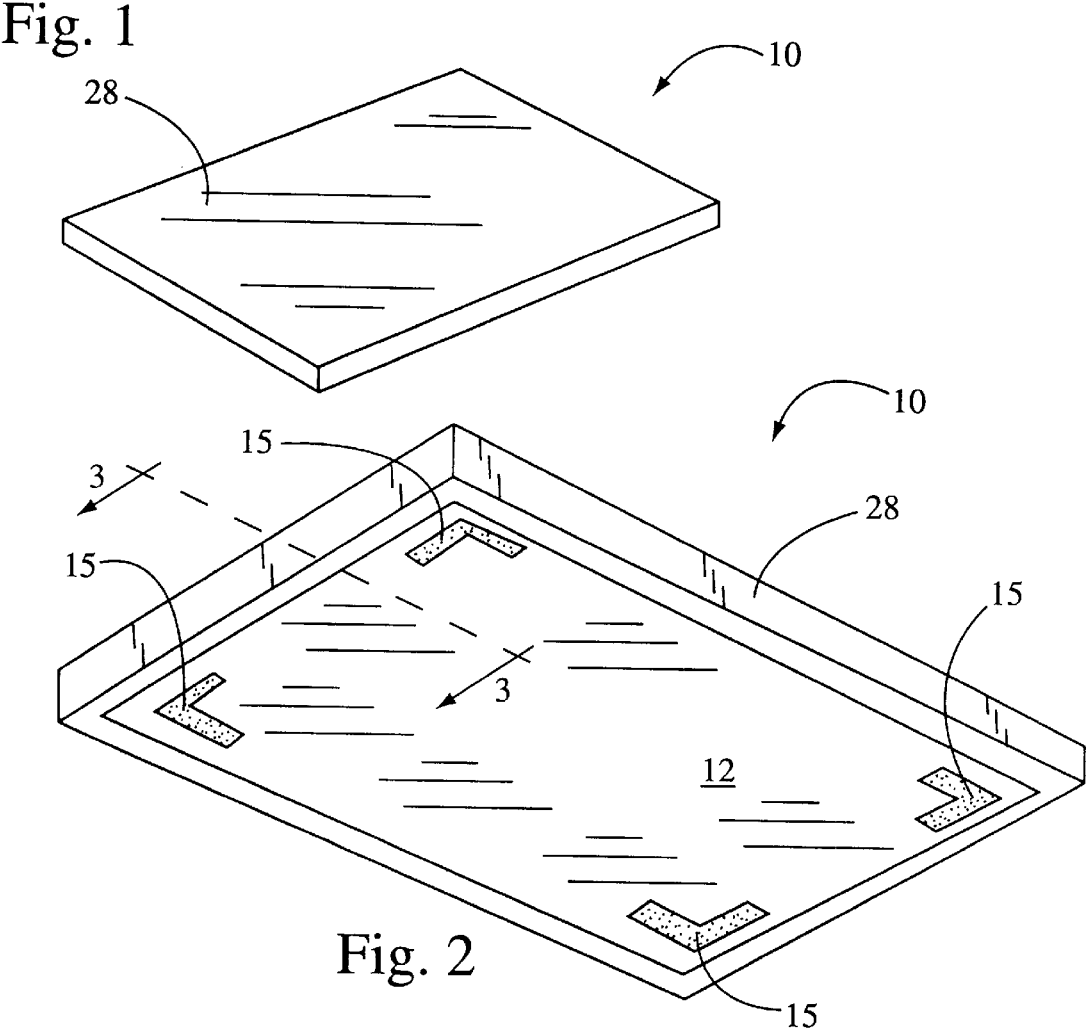
Fig. 1
Fig. 2
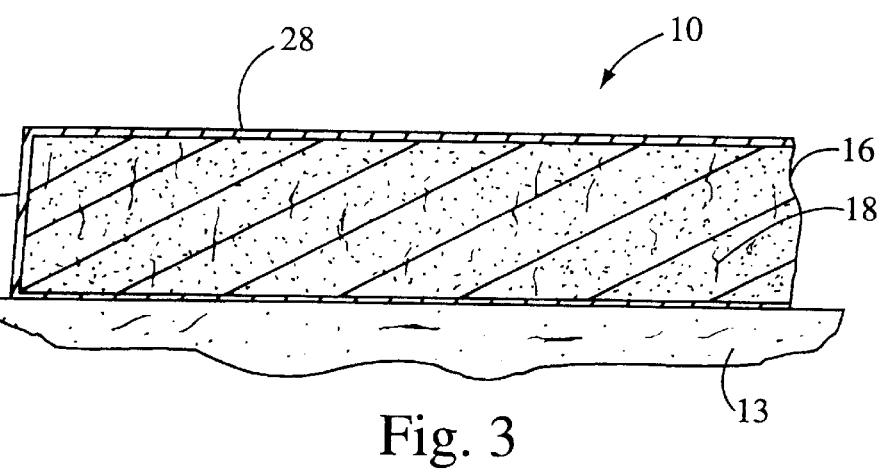
Fig. 3

COMPRESSION SPONGE FOR WOUND CARE

FIELD OF THE INVENTION

The present invention relates in general to wound treatment, and in particular to a generally leak-proof peripherally sealed compression sponge for wound care positionable at a wound site to absorb liquid emanating from the site and having at least one generally uniform bibulous layer operable as a wick to absorb, generally uniformly distribute there through, and retain liquid whereby such uniform liquid distribution throughout the entire layer provides uniform pressure distribution of any externally applied pressure on the pad.

BACKGROUND OF THE INVENTION

Both accidental injuries and medical procedures can involve wounds that produce liquid drainage during a healing process. A non-limiting example of an injury exhibiting such wounds is that of a burn victim whose burned skin area discharges a liquid. Likewise, a non-limiting example of a medical procedure that causes liquid discharge is found in patient recovery from tumescent liposuction procedures involving infusion of relatively large quantities of liquid which then must exit tissue sites. In such liposuction procedures, an elastic garment may be worn over an absorbent medium, but non-uniform distribution of absorbed liquid drainage in such cases can cause bruising of skin tissue.

As is apparent to both the trained medical professional and the general population, it is important to remove drainage liquid in order to promote proper and expedited healing. One manner of accomplishing such removal is to constantly change wound dressings several times a day or even several times an hour. While such an approach may aid in healing, it is obvious that patient mobility must be minimal while patient care requirements are very high. Another approach is to cover wound sites with sterile gauze or similar materials that absorb liquid drainage but do not draw the drainage away from the interfacing location of gauze and wound. Resultantly, the wound site is maintained in a damp condition by the very drainage liquid that the bandage is intended to remove. In liposuction procedures, an elastic garment may be worn over an absorbent prior-art wound dressing, but non-uniform distribution of absorbed liquid drainage within the dressing can cause bruising of skin tissue.

In view of the importance of proper liquid removal from a wound site, it is apparent that a need is present for an absorption medium that effectively and healthfully absorbs and retains liquid drainage. Accordingly, a primary object of the present invention is to provide a compression sponge for collecting wound site liquid and drawing such liquid away from the wound site interface.

Another object of the present invention is to provide a compression sponge for wound care having at least one generally uniform layer operable as a wick to absorb, generally uniformly distribute there through, and retain liquid.

Still another object of the present invention is to provide a compression sponge for wound care having a smooth, uniform surface for compression of skin and operating in cooperation with a uniform pressure distribution throughout the pad in order to minimize bruising of skin that overlies compartments of fat treated by tumescent liposuction.

Yet another object of the present invention is to provide a compression sponge for wound care capable of leak-proof retention of liquid.

These and other objects of the present invention will become apparent throughout the description thereof which now follows.

SUMMARY OF THE INVENTION

The present invention is a compression sponge for wound care operable in the collection of liquid emanating from a wound site. The pad has at least one generally uniform bibulous layer operable as a wick to absorb, generally uniformly distribute there through, and retain liquid whereby such uniform liquid distribution throughout the entire layer provides uniform pressure distribution of any externally applied pressure on the pad. A liquid-permeable sheet such as a non-interacting, liquid-permeable paper product is disposed on the surface of the bibulous layer to interface with the wound site, while a liquid impermeable sheet with wrap-around edges prevents leakage of liquid from the pad.

Preferably, the liquid-permeable sheet of the pad in contact with a wound site is generally non-adherable in and of itself to the wound site. Depending upon the type of wound being treated, minimal adhesive material can be provided such as small pieces of double-faced tape placed on the sheet. The bibulous layer can be provided with an antibacterial agent, with a pattern such as a waffle contour for greater comfort especially for burn wounds, and/or with a thicknesses exhibiting desired characteristics of porosity, density, and the like in accord with optimum wound treatment. In particular, a smooth, unwrinkled, compressible layer can significantly contribute toward reduction of bruising while simultaneously effectively absorbing liquid drainage from a surgical wound site. Further, because the bibulous layer is a wick, liquid absorbed therein quickly disperses throughout the layer to result in uniform liquid distribution throughout the entire layer such that any externally applied pressure any place on the pad transfers to uniform pressure distribution throughout the pad. Such pressure distribution is particularly important in the treatment of tumescent drainage after liposuction since a tight elastic garment is worn over strategically placed pads. Because pressure from the garment is distributed evenly throughout the pad as opposed to being concentrated at its site of origin, patient bruising is reduced or eliminated. The pad of the present invention thus provides a therapeutic benefit in the healing of external and subcutaneous wounds, whether caused by medical procedures or by injurious events.

BRIEF DESCRIPTION OF THE DRAWINGS

An illustrative and presently preferred embodiment of the invention is shown in the accompanying drawings in which:

FIG. 1 is a perspective view of the upper surface of a compression sponge for wound care;

FIG. 2 is a perspective view of the lower surface of the compression sponge of FIG. 1; and FIG. 3 is a partial side elevation view of the compression sponge of FIG. 1 in section along line 3—3 of FIG. 2.

DETAILED DESCRIPTION OF THE PREFERRED EMBODIMENT

Referring to FIGS. 1–3, a compression sponge 10 for placement at a wound site on the skin of a person is shown. The pad 10 has a lower cover sheet 12 which is in contact and interfaces with the skin 13 when the pad 10 is in use, and is constructed of conventional absorbent paper through which liquid can pass. The cover sheet 12 can be provided with small pieces 15 of double-faced adhesive for adhesion of the pad 10 to wound-site skin if that skin is not too sensitive for such adhesive action. Otherwise, the pad 10 can be provided without adhesive pieces 15 and is retained in place with adhesive tape strips applied externally, with a dressing-covering, with a tight-fitting overlay elastic garment, or with any other appropriate retainer as would be recognized in the art. As earlier related, the post-treatment of liposuction procedures on a patient can be effectively accomplished by applying pad(s) 10 at the site(s) of liquid drainage and then having the patient wear an elastic garment (not shown) over the pad(s) 10. Because of the characteristics of the layer 16, described below, with respect to generally uniform distribution of absorbed liquid therein, pressure generated by the elastic garment against the pad 10 likewise is generally uniformly distributed to thereby reduce the potential for bruising of affected skin of the patient during liquid drainage.

Immediately behind the sheet cover 12 of absorbent paper is a bibulous layer 16 constructed of a thickness of conventional super absorbent woven fibers 18 networked to draw liquid in wick-like fashion to thereby quickly distribute absorbed liquid generally uniformly. The layer 16 can be provided with an antibacterial agent to prevent organism growth. Physical configuration of the surface of the layer 16 can be smooth as shown, which aids in preventing bruising as earlier noted, or it can be of a pattern such as a waffle or other design which may be more comfortable and provides for better air circulation for sensitive wounds such as those suffered by burn victims. Depending upon the requirements of treatment for particular wounds, various thicknesses of layer 16 can be provided to include different characteristics with respect to porosity, density, reservoir capacity, and the like.

Immediately behind the bibulous layer 16 is a generally formless pliable plastic film 28 that is impervious to liquid passage. The film 28 extends on all four sides of the pad 10 as shown best in FIG. 2 beyond the respective edges of the bibulous layer 16 and wraps around the borders to be bonded as known in the art to the perimeter of the cover sheet 12. Such construction can alleviate liquid leakage from the perimeter of the pad 10.

In use, the pad 10 is placed over a wound, and can be held in place by an overlaying elastic garment (not shown), by adhesive tape strips (not shown) bridging from the pad to surrounding skin, by adhesive double-faced tape pieces 15 applied minimally as described above and illustrated in FIG. 2, or by any other dressing method as recognized in the art. Thus, if the pad is used to treat the site of a burn, minimal or no adhesive material is used, and the pad is held in place in any manner that a physician determines as most comfortable for a patient. The pads 10 have special utility in the treatment of liposuction recovery where favorable tumescent methodology has been employed. Because this methodology includes sub-cutaneous infusion of a large quantity of liquid which must be expelled after the liposuction procedure is completed, the high reservoir capacity and wicking action found in the pads beneficially accomplish liquid removal directly from skin sites where liposuction has been performed by retaining pads 10 in place with a tight-fitting elastic garment. Because the pad 10 has sealed edges, it is especially amenable to use under a garment since no leakage occurs from the edges of the pad 10 while a user moves about in normal activities. Absorbed liquid rapidly travels throughout the layer 16 because of wicking action to thereby provide a generally uniformly pressure-reactant pad 10 throughout which externally applied pressure, such as by an elastic garment, is uniformly distributed throughout the pad 10 to thereby evenly distribute such pressure to the patient while accomplishing reduced bruising and effective drainage control. Because one or more pads 10, as needed, effectively draw weeping liquid away from a wound site while providing a generally uniform pressure in accord with pressure generated by an external source at one area of the pad 10, the pads 10 enhance comfort, convenience and healing.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

I claim:

1. A compression sponge for wound care, the sponge comprising:
    a) at least one generally uniform bibulous layer operable as a wick to absorb, generally uniformly distribute there through, and retain liquid whereby such uniform liquid distribution throughout the entire layer provides uniform pressure distribution of any externally applied pressure on the pad;
    b) a liquid permeable sheet disposed on a first surface of the bibulous layer; and
    c) a liquid impermeable sheet disposed on a second surface of the bibulous layer opposite the first surface, wherein the liquid impermeable sheet extends along and in vertical contact with all vertical edges of the bibulous layer and is folded over and attached along all perimeter borders of the liquid permeable sheet.

2. A compression sponge for wound care as claimed in claim 1 wherein the liquid permeable sheet is a non-interacting, liquid-permeable paper product.

3. A compression sponge for wound care as claimed in claim 1 wherein the bibulous layer is provided with an antibacterial agent.

4. A compression sponge for wound care as claimed in claim 1 wherein the liquid impermeable sheet is constructed of a formless plastic film.

5. A compression sponge for wound care as claimed in claim 1 wherein the bibulous layer is constructed of networked super absorbent woven fibers.

6. A method for collecting liquid emanating from a wound site, the method comprising:
    a) placing a compression sponge on the wound site, said pad comprising:
        1) at least one generally uniform bibulous layer operable as a wick to absorb, generally uniformly distribute there through, and retain liquid whereby such uniform liquid distribution throughout the entire layer provides uniform pressure distribution of any externally applied pressure on the pad;
        2) a liquid permeable sheet disposed on a first surface of the bibulous layer; and
        3) a liquid impermeable sheet disposed on a second surface of the bibulous layer opposite the first surface, wherein the liquid impermeable sheet extends along all edges of the bibulous layer and is attached along all perimeter borders of the liquid permeable sheet; and
    b) removing said pad when it becomes saturated with liquid.

7. A method for collecting liquid emanating from a wound site as claimed in claim 6 wherein the liquid permeable sheet of the compression sponge is a non-interacting, liquid-permeable paper product.

8. A method for collecting liquid emanating from a wound site as claimed in claim 6 wherein the bibulous layer is provided with an antibacterial agent.

9. A method for collecting liquid emanating from a wound site as claimed in claim 6 wherein the liquid impermeable sheet is constructed of a formless plastic film.

10. A method for collecting liquid emanating from a wound site as claimed in claim 6 wherein the bibulous layer is constructed of networked super absorbent woven fibers.

11. A method for collecting liquid emanating from a wound site, the method comprising:
   a) placing a compression sponge on the wound site, said pad comprising:
      1) at least one generally uniform bibulous layer operable as a wick to absorb, generally uniformly distribute there through, and retain liquid whereby such uniform liquid distribution throughout the entire layer provides uniform pressure distribution of any externally applied pressure on the pad;
      2) a liquid permeable sheet disposed on a first surface of the bibulous layer; and
      3) a liquid impermeable sheet disposed on a second surface of the bibulous layer opposite the first surface, wherein the liquid impermeable sheet extends along and in vertical contact with all vertical edges of the bibulous layer and is folded over and attached along all perimeter borders of the liquid permeable sheet; and
   b) removing said pad when it becomes saturated with liquid.

12. A method for collecting liquid emanating from a wound site as claimed in claim 11 wherein the liquid permeable sheet of the compression sponge is a non-interacting, liquid-permeable paper product.

13. A method for collecting liquid emanating from a wound site as claimed in claim 11 wherein the bibulous layer is provided with an antibacterial agent.

14. A method for collecting liquid emanating from a wound site as claimed in claim 11 wherein the liquid impermeable sheet is constructed of a formless plastic film.

15. A method for collecting liquid emanating from a wound site as claimed in claim 11 wherein the bibulous layer is constructed of networked super absorbent woven fibers.

\* \* \* \* \*

UNITED STATES PATENT AND TRADEMARK OFFICE
CERTIFICATE OF CORRECTION

PATENT NO.   : 6,162,960
DATED        : December 19, 2000
INVENTOR(S)  : Klein

It is certified that error appears in the above-identified patent and that said Letters Patent is hereby corrected as shown below:

Column 4,
Line 46-65, Claim 6 should read as follows:

-- 6. A method for collecting liquid emanating from a wound site, the method comprising:
    a) placing a compression sponge on the wound site, said pad comprising:
        1) at least one generally uniform bibulous layer operable as a wick to absorb, generally uniformly distribute there through, and retain liquid whereby such uniform liquid distribution throughout the entire layer provides uniform pressure distribution of any externally applied pressure on the pad;
        2) a liquid permeable sheet disposed on a first surface of the bibulous layer; and
        3) a liquid impermeable sheet disposed on a second surface of the bibulous layer opposite the first surface, wherein the liquid impermeable sheet extends along and in vertical contact with all vertical edges of the bibulous layer and is folded over and attached along all perimeter borders of the liquid permeable sheet; and
    b) removing said pad when it becomes saturated with liquid. --

Signed and Sealed this

Eleventh Day of March, 2003

JAMES E. ROGAN
*Director of the United States Patent and Trademark Office*